United States Patent [19]
Rudie et al.

[11] Patent Number: 5,464,445
[45] Date of Patent: * Nov. 7, 1995

[54] DEVICE AND METHOD FOR ASYMMETRICAL THERMAL THERAPY WITH HELICAL DIPOLE MICROWAVE ANTENNA

[75] Inventors: Eric N. Rudie, Plymouth; Bruce H. Neilson, Brooklyn Park; James V. Kauphusman, Champlin, all of Minn.

[73] Assignee: Urologix, Inc., Minneapolis, Minn.

[ * ] Notice: The portion of the term of this patent subsequent to May 9, 2012, has been disclaimed.

[21] Appl. No.: 208,642

[22] Filed: Mar. 9, 1994

Related U.S. Application Data

[63] Continuation of Ser. No. 847,718, Mar. 6, 1992.
[51] Int. Cl.⁶ .................................................. A61N 5/02
[52] U.S. Cl. ........................ 607/101; 607/102; 607/105; 607/113; 607/116; 607/156
[58] Field of Search ................................. 607/100–102, 607/105, 113, 116, 154, 156

[56] References Cited

U.S. PATENT DOCUMENTS

| | | |
|---|---|---|
| 2,407,690 | 9/1946 | Southworth . |
| 3,125,096 | 3/1964 | Antiles et al. . |
| 3,228,400 | 1/1966 | Armao . |
| 3,494,723 | 2/1970 | Gray . |
| 3,997,408 | 8/1976 | MacKew ........................... 128/349 |
| 4,140,130 | 2/1979 | Storm, III .......................... 128/404 |
| 4,154,246 | 5/1979 | LeVeen ............................. 128/784 |
| 4,162,500 | 7/1979 | Jacobi et al. ...................... 343/772 |
| 4,204,549 | 5/1980 | Paglione ........................... 128/784 |
| 4,311,154 | 1/1982 | Sterzer et al. .................... 128/804 |
| 4,375,220 | 3/1983 | Matvias ............................. 128/804 |

(List continued on next page.)

FOREIGN PATENT DOCUMENTS

| | | |
|---|---|---|
| 0105677A1 | 4/1984 | European Pat. Off. . |
| 0246176A2 | 11/1987 | European Pat. Off. . |
| 0248758A1 | 12/1987 | European Pat. Off. . |
| 0253677 | 1/1988 | European Pat. Off. . |
| 0311295A2 | 4/1989 | European Pat. Off. . |
| 0335022A1 | 10/1989 | European Pat. Off. . |
| 0341988A1 | 11/1989 | European Pat. Off. . |
| 0370890A1 | 5/1990 | European Pat. Off. . |
| 0449472A1 | 10/1991 | European Pat. Off. . |
| 0459535A2 | 12/1991 | European Pat. Off. . |

(List continued on next page.)

OTHER PUBLICATIONS

Adam et al., "VIIth Meeting of the European Society for Hyperthermic Oncology (ESHO), Paris, Sep. 16–18, 1985," *Strahlentherapie*, vol. 161, No. 9, pp. 523–557 (1985).

M. Astrahan et al., "Thermometry Characteristics of the BSD Interstitial Hyperthermia Applicator," *Endocurie, Hypertherm, Oncol.*, vol. 3, pp. 153–160 (Jul. 1987).

M. Astrahan et al., "Heating Characteristics of a Helical Microwave Applicator for Transurethral Hyperthermia of Benign Prostatic Hyperplasia," *Int. J. Hyperthermia*, vol. 7, No. 1, pp. 141–155 (1991).

(List continued on next page.)

Primary Examiner—Lee S. Cohen
Attorney, Agent, or Firm—Kinney & Lange

[57] ABSTRACT

An intraurethral, Foley-type catheter shaft contains a microwave antenna capable of generating a cylindrically symmetrical thermal pattern, within which temperatures are capable of exceeding 45° C. The antenna, which is positioned within the shaft, is surrounded by means within the shaft for absorbing thermal energy conducted by the tissue and asymmetrically absorbing electromagnetic energy emitted by the antenna—a greater amount of electromagnetic energy being absorbed on one side of the shaft. This asymmetrical absorption alters the thermal pattern generated by the microwave antenna, making it cylindrically asymmetrical, which effectively focuses microwave thermal therapy toward undesirous benign tumorous tissue growth of a prostate anterior and lateral to the urethra, and away from healthy tissue posterior to the urethra.

4 Claims, 6 Drawing Sheets

U.S. PATENT DOCUMENTS

| | | | |
|---|---|---|---|
| 4,423,725 | 1/1984 | Baran et al. | 128/207.15 |
| 4,469,103 | 9/1984 | Barrett | 128/400 |
| 4,497,324 | 2/1985 | Sullivan et al. | 128/736 |
| 4,589,423 | 5/1986 | Turner | 128/804 |
| 4,601,296 | 7/1986 | Yerushalmi | 128/804 |
| 4,612,940 | 9/1986 | Kasevich et al. | 128/804 |
| 4,632,127 | 12/1986 | Sterzer | 128/804 |
| 4,643,186 | 2/1987 | Rosene et al. | 128/303.1 |
| 4,662,383 | 5/1987 | Sogawa et al. | 128/784 |
| 4,672,963 | 6/1987 | Barken | 128/303.1 |
| 4,672,980 | 6/1987 | Turner | 128/804 |
| 4,676,258 | 6/1987 | Inokuchi et al. | 128/804 |
| 4,681,122 | 7/1987 | Winters et al. | 128/736 |
| 4,690,156 | 9/1987 | Kikuchi et al. | 128/804 |
| 4,700,716 | 10/1987 | Kasevich et al. | 128/804 |
| 4,709,698 | 12/1987 | Johnston et al. | 128/303.12 |
| 4,732,161 | 3/1988 | Azam et al. | 128/784 |
| 4,776,086 | 10/1988 | Kasevich et al. | 29/828 |
| 4,800,899 | 1/1989 | Elliott | 128/804 |
| 4,808,164 | 2/1989 | Hess | 604/95 |
| 4,813,429 | 3/1989 | Eshel et al. | 128/736 |
| 4,821,725 | 4/1989 | Azam et al. | 128/420 |
| 4,823,812 | 4/1989 | Eshel et al. | 128/804 |
| 4,825,880 | 5/1989 | Stauffer et al. | 128/804 |
| 4,832,023 | 5/1989 | Murphy-Chutorian et al. | 128/303.1 |
| 4,841,988 | 6/1989 | Fetter et al. | 128/804 |
| 4,856,528 | 8/1989 | Yang et al. | 128/653 |
| 4,865,047 | 9/1989 | Chou et al. | 128/784 |
| 4,869,259 | 9/1989 | Elkins | 128/660 |
| 4,907,589 | 3/1990 | Cosman | 606/34 |
| 4,924,863 | 5/1990 | Sterzer | 606/27 |
| 4,955,377 | 9/1990 | Lennox et al. | 128/401 |
| 4,967,765 | 11/1990 | Turner et al. | 128/785 |
| 4,993,430 | 2/1991 | Shimoyama et al. | 128/784 |
| 4,998,933 | 3/1991 | Eggers et al. | 606/41 |
| 5,003,991 | 4/1991 | Takayama et al. | 128/784 |
| 5,007,437 | 4/1991 | Sterzer | 428/786 |
| 5,026,959 | 6/1991 | Ito et al. | 219/10.55 |
| 5,037,395 | 8/1991 | Spencer | 604/113 |
| 5,045,056 | 9/1991 | Behl | 604/49 |
| 5,056,531 | 10/1991 | Shimoyama | 128/784 |
| 5,057,106 | 10/1991 | Kasevich et al. | 606/33 |
| 5,061,267 | 10/1991 | Zeiher | 606/40 |
| 5,097,845 | 3/1992 | Fetter et al. | 128/804 |
| 5,106,360 | 4/1992 | Ishiwara et al. | 600/2 |
| 5,151,100 | 9/1992 | Abele et al. | 606/28 |
| 5,220,927 | 6/1993 | Astrahan et al. | 128/785 |
| 5,234,004 | 8/1993 | Hascoet et al. | 607/116 |
| 5,249,585 | 10/1993 | Turner et al. | 607/99 |
| 5,304,214 | 4/1994 | DeFord et al. | 607/105 |
| B1 4,841,988 | 8/1990 | Fetter et al. | 128/804 |

FOREIGN PATENT DOCUMENTS

| | | | |
|---|---|---|---|
| 2407559A1 | 8/1975 | German Dem. Rep. | |
| 3011322A1 | 9/1980 | Germany | 3/2 |
| 3525702A1 | 1/1987 | Germany | |
| 3730494A1 | 3/1988 | Germany | |
| 3725691A1 | 3/1988 | Germany | |
| 738596 | 6/1980 | U.S.S.R. | |
| 1266548A1 | 5/1985 | U.S.S.R. | |
| 1512622A1 | 10/1989 | U.S.S.R. | |
| 1563795 | 4/1980 | United Kingdom | 7/12 |
| WO81/03616 | 12/1981 | WIPO | |
| WO86/09191 | 3/1986 | WIPO | |
| WO86/05990 | 10/1986 | WIPO | |
| WO89/02292 | 3/1989 | WIPO | |
| WO89/05609 | 6/1989 | WIPO | |
| WO89/07909 | 9/1989 | WIPO | |
| WO89/11311 | 11/1989 | WIPO | |
| WO90/13333 | 11/1990 | WIPO | |
| WO91/11975 | 8/1991 | WIPO | |
| WO91/13650 | 9/1991 | WIPO | |
| WO91/15174 | 10/1991 | WIPO | |
| WO91/15154 | 10/1991 | WIPO | |
| 9210142 | 5/1992 | WIPO | |
| 9404220 | 3/1994 | WIPO | |

OTHER PUBLICATIONS

I. A. Brezovich et al., "A Practical System for Clinical Radiofrequency Hyperthermia," *Int. J. Radiation Oncology Biol. Phys.*, vol. 7, No. 3, pp. 423–430 (Mar. 1981).

R. T. Constable et al., "Perturbation of the Temperature Distribution in Microwave Irradiated Tissue Due to the Presence of Metallic Thermometers," *Med. Phys.*, vol. 14, No. 3, pp. 385–387 (May/Jun. 1987).

P. B. Dunscombe et al., "Heat Production in Microwave–Irradited Thermocouples," *Med. Phys.*, vol. 13, No. 4, pp. 457–461 (Jul./Aug. 1986).

A. Ghods et al., "An Insulated Coaxial Probe for EM Local Heating," *IEEE Transactions on Biomedical Engineering*, vol. BMF–32, No. 6, pp. 418–427 (Jun. 1985).

B. Giovanella et al., "Selective Lethal Effect of Supranormal Temperatures on Human Neoplastic Cells," *Cancer Research*, vol. 36, pp. 3944–3950 (Nov. 1976).

T. Harada et al., "Microwave Surgical Treatment of Diseases of Prostate," *Urology*, vol. 26, No. 6, pp. 572–576 (Dec. 1985).

T. Harada et al., "Microwave Surgical Treatment of the Prostate: Clinical Application of Microwave Surgery as a Tool for Improved Prostatic Electroresection," *Urol. Int.*, vol. 42, pp. 127–131 (1987).

T. Harada et al., "Intraoperative Real–Time Ultrasonic Scanning for Microwave Coagulation of the Prostate," *Urol. Radiol.*, vol. 12, pp. 45–49 (1990).

T. Harada et al., "Remote Afterloading Transurethral Radiotherapy for Prostatic Cancer," *Urol. Int.*, vol. 45, pp. 41–43 (1990).

*The Journal of Urology*, vol. 135, No. 4, Part 2, pp. 339A, 247A, 338A (Apr. 1986).

*The Journal of Urology*, No. 4, Part 2, p. 358A (Apr. 1987).

D–J. Lee et al., "Design and Thermometry of an Intracavitary Microwave Applicator Suitable for Treatment of Some Vaginal and Rectal Cancers," *Int. J. Radiation Oncology Biol. Phys.*, vol. 10, No. 11, pp. 2155–2162 (Nov. 1984).

D–J. Lee et al., "A New Design of Microwave Interstitial Applicators for Hyperthermia With Improved Treatment Volume," *Int. J. Radiation Oncology Biol. Phys.*, vol. 12, No. 11, pp. 2003–2008 (Nov. 1986).

Leybovich et al., "Intracavitary Hyperthermia: A Newly Designed Applicator for Tracheal Tumors," *Endocurie, Hypertherm, Oncol.*, vol. 3, pp. 23–29 (Jan. 1987).

M. Manning et al., "Clinical Hyperthermia: Results of a Phase I Trial Employing Hyperthermia Alone or in Combination With External Beam or Interstitial Radiotherapy," *Cancer*, vol. 49, pp. 205–216 (1982).

J. Marmor et al., "Combined Radiation and Hyperthermia in Superficial Human Tumors," *Cancer*, vol. 46, pp. 1986–1991 (Nov. 1, 1980).

McNeal, Stamey and Hodge, *1988 Monographs in Urology*, vol. 9, No. 3, pp. 35–53.

J. Mendecki et al., "Microwave Applicators for Localized Hyperthermia Treatment of Cancer of the Prostate," *Int. J. Radiation Oncology Biol. Phys.*, vol. 6, No. 11, pp. 1583–1588 (Nov. 1980).

J. Overgaard, "Fractionated Radiation and Hyperthermia:

Experimental and Clinical Studies," *Cancer*, vol. 48, pp. 1116–1123 (1981).

V. Sathiaseelan et al., "A Clinical Microwave Hyperthermia System With Multipoint Real–Time Thermal Dosimetry," *The British Journal of Radiology*, vol. 58, pp. 1187–1195 (Dec. 1985).

S. Tsuchida et al., "A New Modified Catheter for Voiding Cystourethrography," *Tohoku J. exp. Med.*, vol. 138, pp. 289–298 (1982).

P. F. Turner, "Recent Developments and Work in Progress," *Strahlentherapie und Onkologie*, vol. 163, No. 7, pp. 442–444 (1987).

Valdagni et al., "Clinical Hyperthermia: Five Year's Experience," *Strahlentherapie und Onkologie*, vol. 163, No. 7, pp. 443–445 (1987).

A. Wu et al., "Performance Characteristics of a Helical microwave Interstitial Antenna for Local Hyperthermia," *Med. Phys.*, vol. 14, No. 2, pp. 235–237 (Mar./Apr. 1987).

A. Yerushalmi, "Combined Treatment of a Solid Tumour by Local Hyperthermia and Actinomycin D," *Br. J. Cancer*, vol. 37, 827–832 (1978).

Yerushalmi et al., "Local Microwave Hyperthermia in the Treatment of Carcinoma of the Prostate," *Oncology*, vol. 43, pp. 299–305 (1986).

A. Yerushalmi, "Localized, Non–Invasive Deep Microwave Hyperthermia for the Treatment of Prostatic Tumors: The First 5 Years," *Recent Results in Cancer Research*, vol. 107, pp. 141–146 (1988).

A. Yerushalmi, "Use of Local Hyperthermia for the Treatment of Benign Prostatic Hyperplasia," *Consensus on Hyperthermia for the 1990s*, pp. 167–176 (Plenum Press, New York, 1990).

A. Yerushalmi et al., "Localized Deep Microwave Hyperthermia in the Treatment of Poor Operative Risk Patients With Benign Prostatic Hyperplasia," *The Journal of Urology*, vol. 133, pp. 873–876 (May).

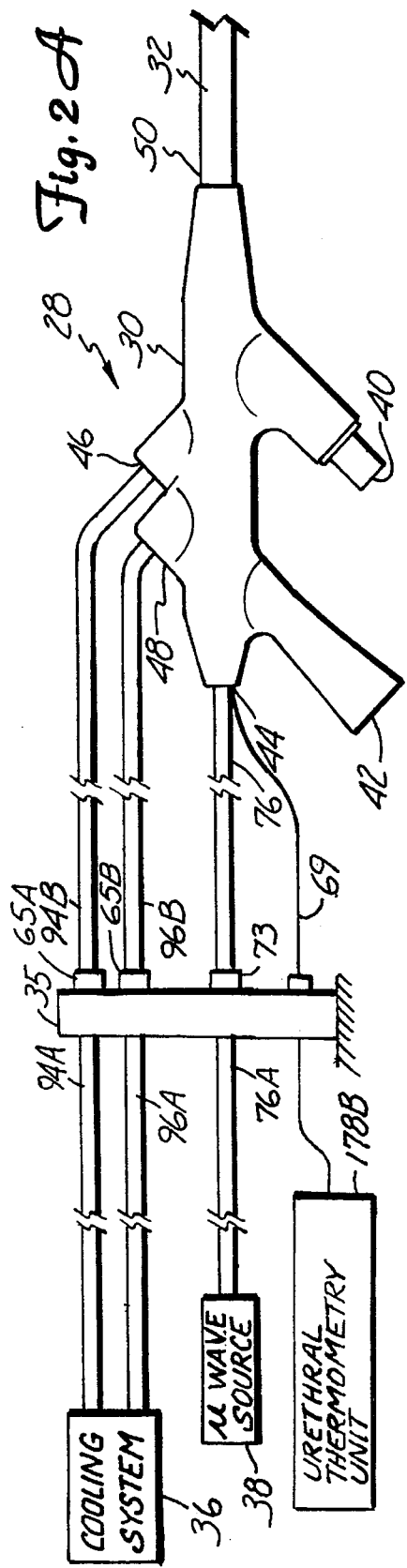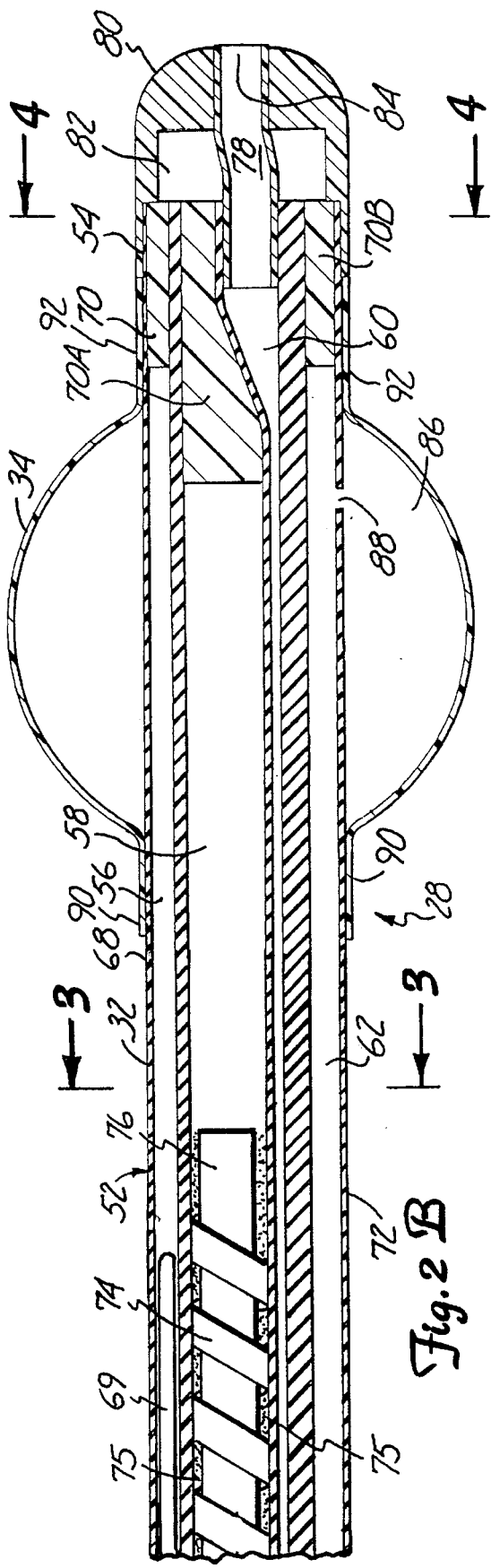

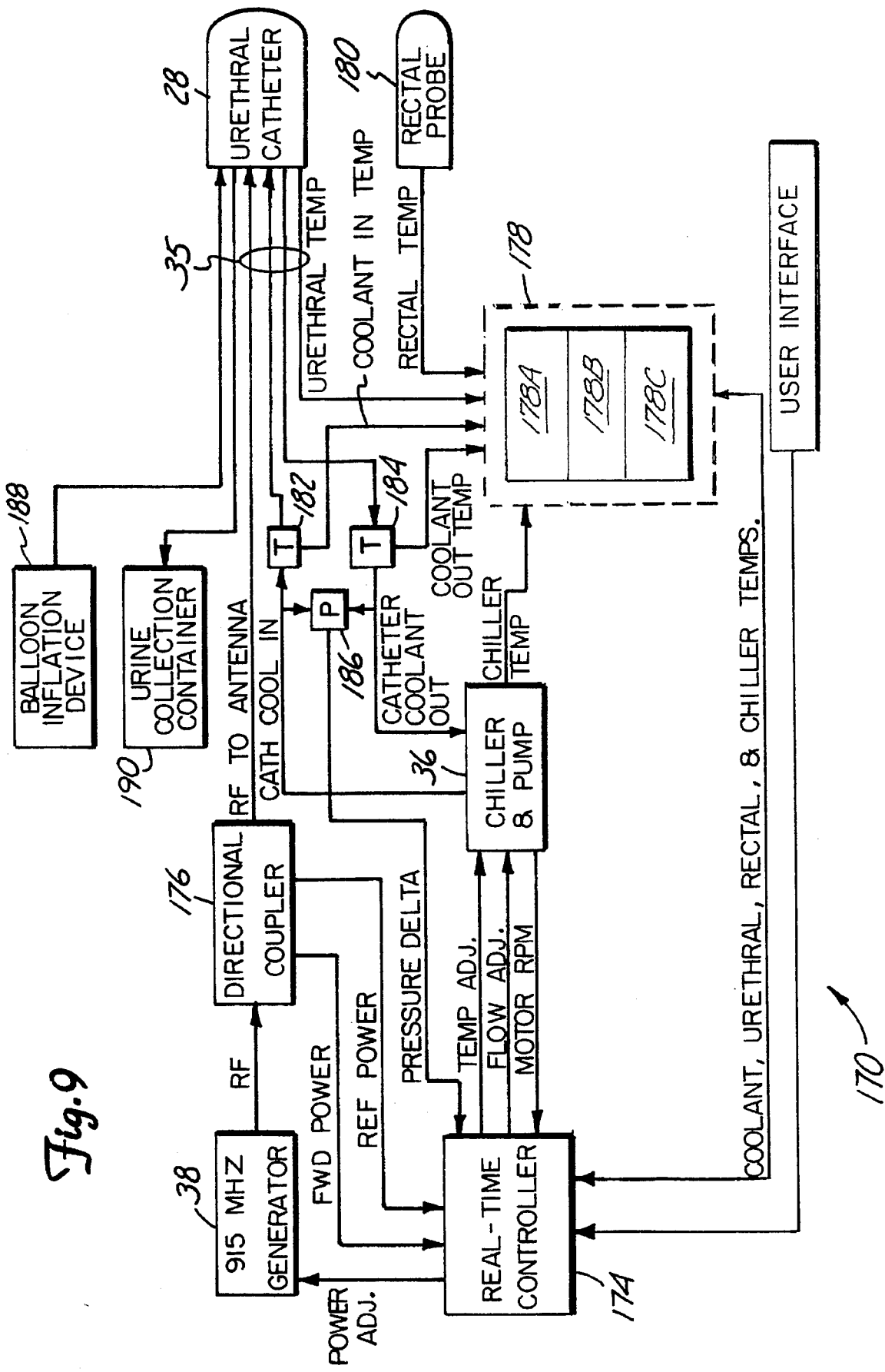

DEVICE AND METHOD FOR ASYMMETRICAL THERMAL THERAPY WITH HELICAL DIPOLE MICROWAVE ANTENNA

This is a continuation of application Ser. No. 07/847,718, filed Mar. 6, 1992.

REFERENCE TO CO-PENDING APPLICATIONS

Reference is made to the following co-pending U.S. Patent application Ser. No. 07/847,915, filed Mar. 6, 1992, entitled GAMMA MATCHED, HELICAL DIPOLE MICROWAVE ANTENNA, by E. Rudie, and Ser. No. 07/847,894, filed Mar. 6, 1992, entitled METHOD FOR TREATING INTERSTITIAL TISSUE ASSOCIATED WITH MICROWAVE THERMAL THERAPY, by B. Neilson et al.

BACKGROUND OF THE INVENTION

The present invention relates to the field of microwave thermal therapy of tissue. In particular, the present invention relates to a catheter for transurethral microwave thermal therapy of benign prostatic hyperplasia (BPH).

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and bladder. The remaining two thirds of the prostate is generally posterior to the urethra and is comprised of glandular tissue.

This relatively small organ, which is the most frequently diseased of all internal organs, is the site of a common affliction among older men: BPH (benign prostatic hyperplasia). BPH is a nonmalignant, bilateral nodular expansion of prostrate tissue in the transition zone, a periurethral region of the prostate between the fibromuscular tissue and the glandular tissue. The degree of nodular expansion within the transition zone tends to be greatest anterior and lateral to the urethra, relative to the posterior-most region of the urethra. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Traditionally, the most frequent treatment for BPH has been surgery (transurethral resection). Surgery, however, is often not an available method of treatment for a variety of reasons. First, due to the advanced age of many patients with BPH, other health problems, such as cardiovascular disease, can warrant against surgical intervention. Second, potential complications associated with transurethral surgery, such as hemorrhage, anesthetic complications, urinary infection, dysuria, incontinence and retrograde ejaculation, can adversely affect a patient's willingness to undergo such a procedure.

A fairly recent alternative treatment method for BPH involves microwave thermal therapy, in which microwave energy is employed to elevate the temperature of tissue surrounding the prostatic urethra above about 45° C., thereby thermally damaging the tumorous tissue. Delivery of microwave energy to tumorous prostatic tissue is generally accomplished by a microwave antenna-containing applicator, which is positioned within a body cavity adjacent the prostate gland. The microwave antenna, when energized, heats adjacent tissue due to molecular excitation and generates a cylindrically symmetrical radiation pattern which encompasses and necroses the tumorous prostatic tissue. The necrosed intraprostatic tissue is subsequently reabsorbed by the body, thereby relieving an individual from the symptoms of BPH.

One method of microwave thermal therapy described in the art includes intrarectal insertion of a microwave antenna-containing applicator. Heat generated by the antenna's electromagnetic field is monitored by a sensor which is positioned near the prostate gland by a urethral catheter. Owing to the distance between the rectum and the tumorous prostatic tissue of the transition zone, however, healthy intervening tissue within the cylindrically symmetrical radiation pattern is also damaged in the course of the intrarectal treatment. Intrarectal microwave thermal therapy applicators are described in the following references: Eshel et al. U.S. Pat. No. 4,813,429; and, A. Yerushalmi et al., *Localized Deep Microwave Hyperthermia in the Treatment of Poor Operative Risk patients with Benign Prostatic Hyperplasia*, 133 JOURNAL OF UROLOGY 873 (1985).

A safer and more efficacious treatment of BPH is transurethral microwave thermal therapy. This method of treatment minimizes the distance between a microwave antenna-containing applicator and the transition zone of the prostate by positioning a Foley-type catheter-bearing applicator adjacent to the prostate gland within the urethra. Due to the close proximity of the microwave antenna to the prostate, a lesser volume of tissue is exposed to the cylindrically symmetrical radiation pattern generated by the microwave antenna, and the amount of healthy tissue necrosed is reduced. Intraurethral applicators of the type described can be found in Turner et al. U.S. Pat. No. 4,967,765 and Hascoet et al. European Patent Application 89403199.6.

While the close proximity of a transurethral microwave thermal therapy applicator to prostatic tissue reduces the amount of damage to healthy tissue, controlling the volume of tissue to be affected by the microwave energy field continues to be problematic. For instance, microwave antennas known in the art have tended to produce electromagnetic fields which affect a volume of tissue, beyond the desired area of treatment, which necroses healthy, normal tissue.

SUMMARY OF THE INVENTION

The present invention is based upon the recognition that in patients suffering from BPH, tumorous tissue growth within the prostate tends to be the greatest in the portion of the transition zone anterior and lateral to the urethra. The present invention is a transurethral thermal therapy catheter for thermal treatment of BPH which is capable of selectively directing microwave energy toward tumorous prostatic tissue growth anterior and lateral to the urethra, while sparing the urethra and healthy tissue posterior to the urethra from thermal damage.

The catheter preferably includes a flexible shaft which contains a multiplicity of lumens that extend the length of the shaft. A relatively large lumen is located eccentric to a longitudinal axis of the shaft, near a first side of the shaft, and is provided for a microwave antenna. The microwave antenna is connected to a microwave generator by a coaxial cable, and is bonded within the antenna lumen. Microwave energy emitted by the antenna is capable of producing a cylindrically symmetrical radiation pattern which is concentrated about the antenna. Temperatures within a target area of the radiation pattern exceed about 45° C., which effectively necrose the irradiated tissue.

Cooling lumens, which communicate at a proximal end of the shaft, encircle the antenna lumen and are circumjacent an outer surface of the shaft. Water intake lumens adjacent the first side of the shaft are relatively narrow in cross-section, while water exhaust lumens adjacent a second side of the shaft are relatively wide in cross-section. Cooled water from a cooling system is pumped into the water intake lumens at a distal end of the shaft. The water flows to the proximal end of the shaft and returns to the cooling system via the water exhaust lumens. The water within the cooling lumens protects tissue immediately adjacent the outer surface of the shaft when the antenna is energized by absorbing heat energy from the adjacent tissue (i.e. thermal conduction). The water within the cooling lumens also alters the radiation pattern generated by the antenna by absorbing some of the microwave energy emitted by the antenna. Water in the wider exhaust lumens near the second side of the shaft absorbs a greater amount of microwave energy than water in the narrower intake lumens near the first side of the shaft. As a result, the radiation pattern generated by the microwave antenna (and therefore the pattern of thermal energy delivered) becomes asymmetrical, with a target area of tissue adjacent the first side of the shaft being heated above about 45° C., and the tissue adjacent the second side of the shaft remaining below about 45° C.

BRIEF DESCRIPTION OF THE DRAWINGS

FIG. 2A is a side view of the distal end of the urethral catheter of the present invention.

FIG. 2B is an enlarged sectional view of the proximal end of the urethral catheter of the present invention.

FIG. 9 is a block diagram of the transurethral microwave thermal therapy system of the present invention.

DETAILED DESCRIPTION OF THE PREFERRED EMBODIMENTS

Figure 1:
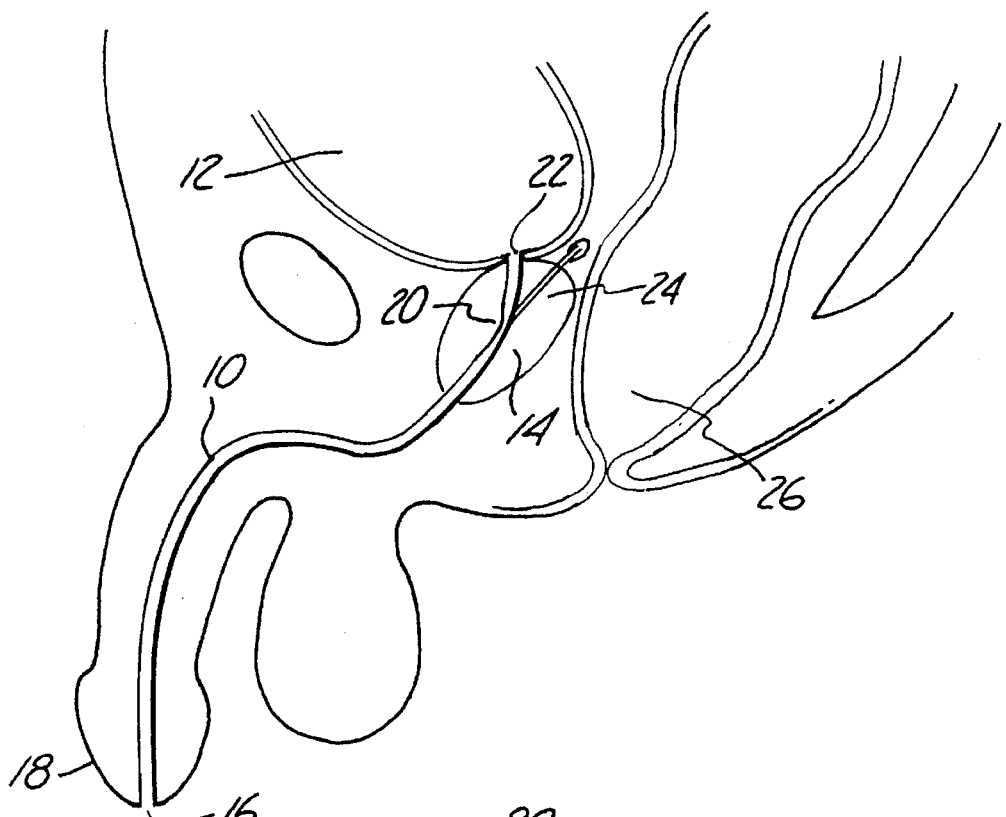
FIG. 1 is a vertical sectional view of a male pelvic region showing the urinary organs affected by benign prostatic hyperplasia.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, only periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. A selective heating of benign tumorous tissue of prostate 14 (transurethral thermal therapy) is made possible by microwave antenna-containing catheter 28 of the present invention, which is shown in FIGS. 2A and 2B.

FIG. 2A shows a side view of a distal end of catheter 28. FIG. 2B shows an enlarged sectional view of a proximal end of catheter 28. As shown in FIGS. 2A and 2B, catheter 28 generally includes multi-port manifold 30, multi-lumen shaft 32, shaft position retention balloon 34, connection manifold 35, cooling system 36 and microwave generating source 38.

Manifold 30 includes inflation port 40, urine drainage port 42, microwave antenna port 44, cooling fluid in port 46 and cooling fluid out port 48. Ports 40–48 communicate with corresponding lumens within shaft 32. Manifold 30 is preferably made of medical-grade silicone sold by Dow Corning under the trademark Silastic Q-7-4850.

Figure 3:
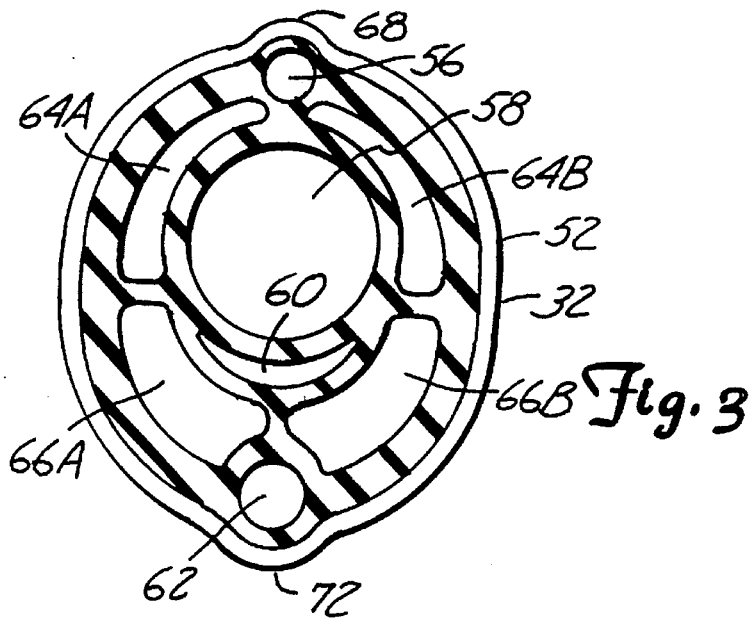
FIG. 3 is a cross-sectional view of the urethral catheter of FIG. 2B taken along line 3—3.

Shaft 32 is connected to manifold 30 at shaft distal end 50. Shaft 32 is a multi-lumen, Foley-type urethral catheter shaft which is extruded from a flexible, medical-grade silicone sold by Dow Corning under the trademark Silastic Q-7-4850. Shaft 32, which has an outer diameter of about 16 French, includes outer surface 52, which is generally elliptical in cross-section as shown in FIG. 3. Shaft 32 is long enough to permit insertion of proximal shaft end 54 through urethra 10 and into bladder 12. In one preferred embodiment, shaft 32 is coated with a hydrophilic solution sold by Hydromer, Inc. under the mark Hydromer, which lubricates outer surface 52 of shaft 32 and facilitates its advancement within urethra 10.

As shown in FIGS. 2B–4, shaft 32 includes temperature sensing lumen 56, microwave antenna lumen 58, urine drainage lumen 60, balloon inflation lumen 62, cooling fluid intake lumens 64A and 64B, and cooling fluid exhaust lumens 66A and 66B. Lumens 56–66B generally extend from distal shaft end 50 to proximal shaft end 54.

Temperature sensing lumen 56 is positioned near first side 68 of shaft 32. Temperature sensing lumen 56 communicates with microwave antenna port 44 and permits insertion of thermometry sensor 69 within shaft 32 to monitor the temperature of surrounding tissue when shaft 32 is inserted within urethra 10. Sensor 69 exits through port 44 and is connected through connection manifold 35 to urethral thermometry unit 178B (shown in FIG. 9). In a preferred embodiment, thermometry sensor 69 is a fiber optic luminescence type temperature sensor sold by Luxtron Corporation. Temperature sensing lumen 56 is sealed at proximal end 54 by silicone plug 70.

Microwave antenna lumen 58 is eccentric to the longitudinal axis of shaft 32, antenna lumen 58 being positioned nearer first side 68 of shaft 32 than second side 72 of shaft 32. Antenna lumen 58 is sealed at proximal end 54 by silicone plug 70A. At its distal end, antenna lumen 58 communicates with microwave antenna port 44. Microwave antenna 74 is permanently positioned within antenna lumen 58 near balloon 34. Antenna 74 is positioned within antenna lumen 58 so as to be generally situated adjacent the benign tumorous tissue of prostate 14 when shaft 32 is properly positioned within urethra 10. As shown in FIGS. 2A–2B, antenna 74 is bonded within antenna lumen 58 by adhesive bond 75. Antenna 74 is carried at the proximal-most end of coaxial cable 76. The distal-most end of coaxial cable 76 is connected to connection manifold 35 by a conventional quick-coupling fitting 73. Coaxial cable 76 communicates with microwave generating source 38 by connection cable 76A, which is connected between microwave generating source 38 and connection manifold 35. In one embodiment, connection cable 76A is a standard RG 400 coaxial cable. Microwave generating source 38 produces a maximum of 100 watts of electrical power at about 915 MHz frequency, +/−13 MHz, which is within the FCC-ISM standards. When antenna 74 is energized by microwave generating source 38, antenna 74 emits electromagnetic energy which causes heating of tissue within prostate 14.

Urine drainage lumen 60 is positioned adjacent antenna lumen 58, between antenna lumen 58 and second side 72. Urine drainage lumen 60 communicates with urine drainage port 42 and defines a drainage path for urine when proximal end 54 of shaft 32 is inserted within bladder 12. Urine drainage lumen 60 is connected to urine drainage lumen extension 78 at proximal end 54. Urine drainage lumen extension 78 is bonded within proximal end cap 80. End cap 80 is further bonded over outer surface 52 of shaft 32 at proximal shaft end 54, with cavity 82 surrounding lumen extension 78. With end cap 80 and urine drainage lumen extension 78 in place, opening 84 to lumen extension 78 permits urine to drain from bladder 12 through urine drainage lumen 60 and out urine drainage port 42 when proximal shaft end 54 is inserted within bladder 12. Drainage of urine from bladder 12 is necessary due to frequent bladder spasms which occur during transurethral thermal therapy.

Balloon inflation lumen 62 is positioned near second side 72, generally between urine drainage lumen 60 and second side 72. Balloon inflation lumen 62 communicates with inflation port 40 and is sealed at proximal end 54 by silicone plug 70B. Balloon inflation lumen 62 communicates with interior 86 of balloon 34 by opening 88.

Figure 5:
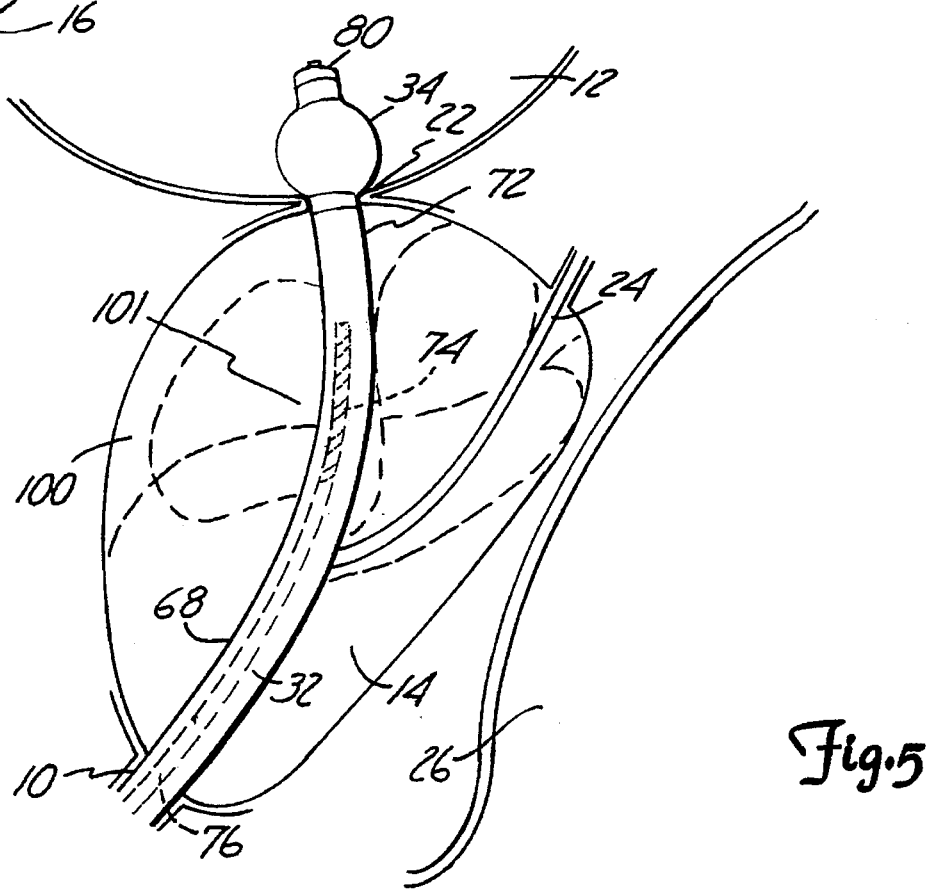
FIG. 5 is an enlarged view of the male pelvic region of FIG. 1 showing the urethral catheter of the present invention positioned within the prostate region.

Balloon 34, which is formed from a tubular section of a flexible, medical-grade silicone sold by Dow Corning under the trademark Silastic Q-7-4720, is secured over shaft 32 by bonding balloon waists 90 and 92 over exterior surface 52 of shaft 32 near proximal shaft end 54. Balloon 34 is inflated by an inflation device 188 (shown in FIG. 9), which is connected to inflation port 40 and which supplies positive fluid pressure to interior 86 of balloon 34. Balloon 34 is deflated when inflation device 188 supplies a negative fluid pressure (i.e., a vacuum) to interior 86 of balloon 34. Balloon 34 serves to retain shaft 32 in a fixed position within urethra 10 when balloon 34 is inflated within bladder 12 near bladder neck 22, as shown in FIG. 5.

As shown in FIGS. 2B–4, cooling fluid intake lumens 64A, 64B are positioned circumjacent first side 68, between first side 68 and antenna lumen 58. Cooling fluid intake lumens 64A, 64B extend from distal shaft end 50 to proximal shaft end 54 where lumens 64A, 64B are exposed to cavity 82 of end cap 80. Intake lumens 64A, 64B are relatively narrow in cross-section and have a relatively small cross-sectional surface area. Water contained within intake lumens 64A, 64B performs two essential functions. First, water contained within lumens 64A, 64B absorbs some of the microwave energy emitted by antenna 74. This assists, in part, in controlling the volume of tissue adjacent first side 68 of shaft 32 that is heated above about 45° C. Second, the water within lumens 64A, 64B absorbs heat energy generated by the microwave energy from adjacent tissues (i.e., urethra 10) via thermal conduction. This prevents the portion of urethra 10 adjacent first side 68 from being overheated and damaged when antenna 74 is energized.

Cooling fluid exhaust lumens 66A, 66B are circumjacent second side 72 with lumens 66A, 66B generally positioned between second side 72 and antenna lumen 58. Like intake lumens 64A, 64B, exhaust lumens 66A, 66B extend from shaft distal end 50 to shaft proximal end 54 where exhaust lumens 66A, 66B are exposed to cavity 82 of end cap 80. Exhaust lumens 66A, 66B are wider in cross-section than intake lumens 64A, 64B, and have a cross-sectional area greater than the cross-sectional area of intake lumens 64A, 64B. Water within exhaust lumens 66A, 66B is therefore capable of absorbing a greater amount of microwave energy when antenna 74 is energized. As a result, for a given power output from microwave generating source 38, the temperature of tissue adjacent second side 72 will remain below about 45° C. Water within exhaust lumens 66A, 66B also absorbs heat energy from adjacent tissue (i.e., urethra 10) when antenna 74 is energized, which prevents the portion of urethra 10 adjacent second side 72 from being overheated and damaged when antenna 74 is energized.

Intake lumens 64A, 64B and exhaust lumens 66A, 66B are supplied with deionized water from cooling system 36. Water from cooling system 36 is chilled to between about 12°–15° C. and pumped at a rate of between about 100–150 milliliters per minute via water feed line 94A to connection manifold 35. The water flows through connection manifold 35 to water feed line 94B and to water intake port 46, which communicates with water intake lumens 64A, 64B. Under fluid pressure, the water circulates through intake lumens 64A, 64B to cavity 82 of end cap 80. The water returns to cooling system 36 through exhaust lumens 66A, 66B to fluid exhaust port 48. The water is carried from water exhaust port 48 via water return line 96B to connection manifold 35, and from connection manifold 35 to cooling system 36 via water return line 96A. The water is then re-chilled and re-circulated. Water feed line 94B and water return line 96B are each provided with a conventional quick-coupling fitting 65A and 65B, respectively, which permits catheter 28 to be easily disconnected from cooling system 36.

Figure 4:
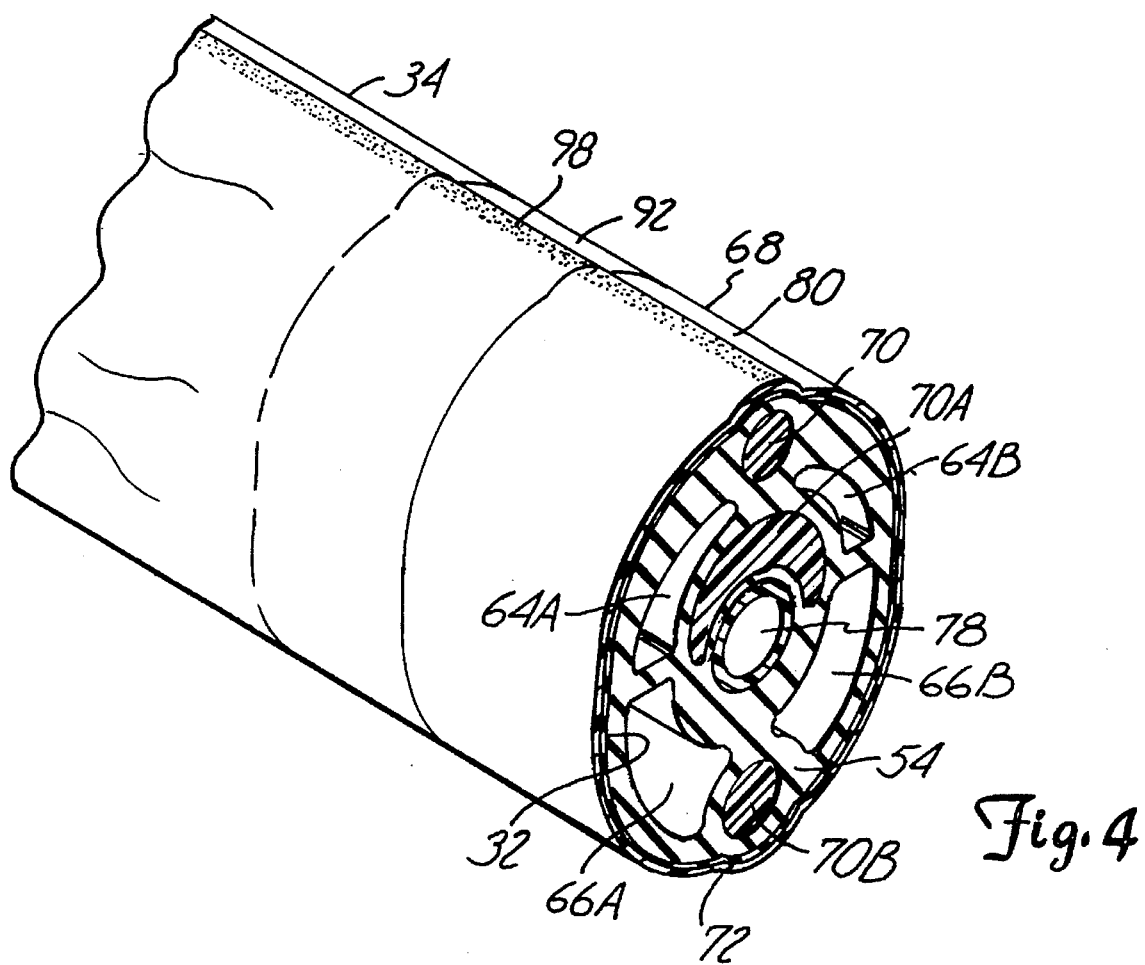
FIG. 4 is a perspective view of a proximal region of the urethral catheter with the end portion taken in section from line 4—4 of FIG. 2B.

FIG. 5 shows an enlarged view of the male pelvic region of FIG. 1 with catheter 28 properly positioned within urethra 10. Orientation stripe 98 along exterior surface 52 on first side 68, as shown in FIG. 4, ensures the proper orientation of shaft 32 within urethra 10. As shown in FIG. 5, shaft 32 is positioned within urethra 10 with second side 72 of shaft 32 oriented toward rectum 26. Water exhaust lumens 66A, 66B are oriented posteriorly, toward rectum 26 and water intake lumens 64A, 64B are oriented anteriorly toward fibromuscular tissue 100 of prostate 14. The portion of transition zone 101 anterior and lateral to urethra 10 is the most frequent location of the tumorous tissue growth which causes BPH. Since water exhaust lumens 66A, 66B are capable of absorbing more microwave energy than water intake lumens 64A, 64B, the radiation patterns created by microwave energy emitted from antenna 74 are asymmetrical. Thus, a relatively large volume of tissue enveloping the anterior portion of transition zone 101, adjacent first side 68, is heated to a temperature above about 45° C., which effectively necroses the tumorous tissue of prostate 14 which encroaches upon urethra 10. In comparison, the temperature of tissue adjacent second side 72 remains below about 45° C., thereby eliminating the harmful effects of the microwave energy to ejaculatory duct 24 and rectum 26.

Figure 6:
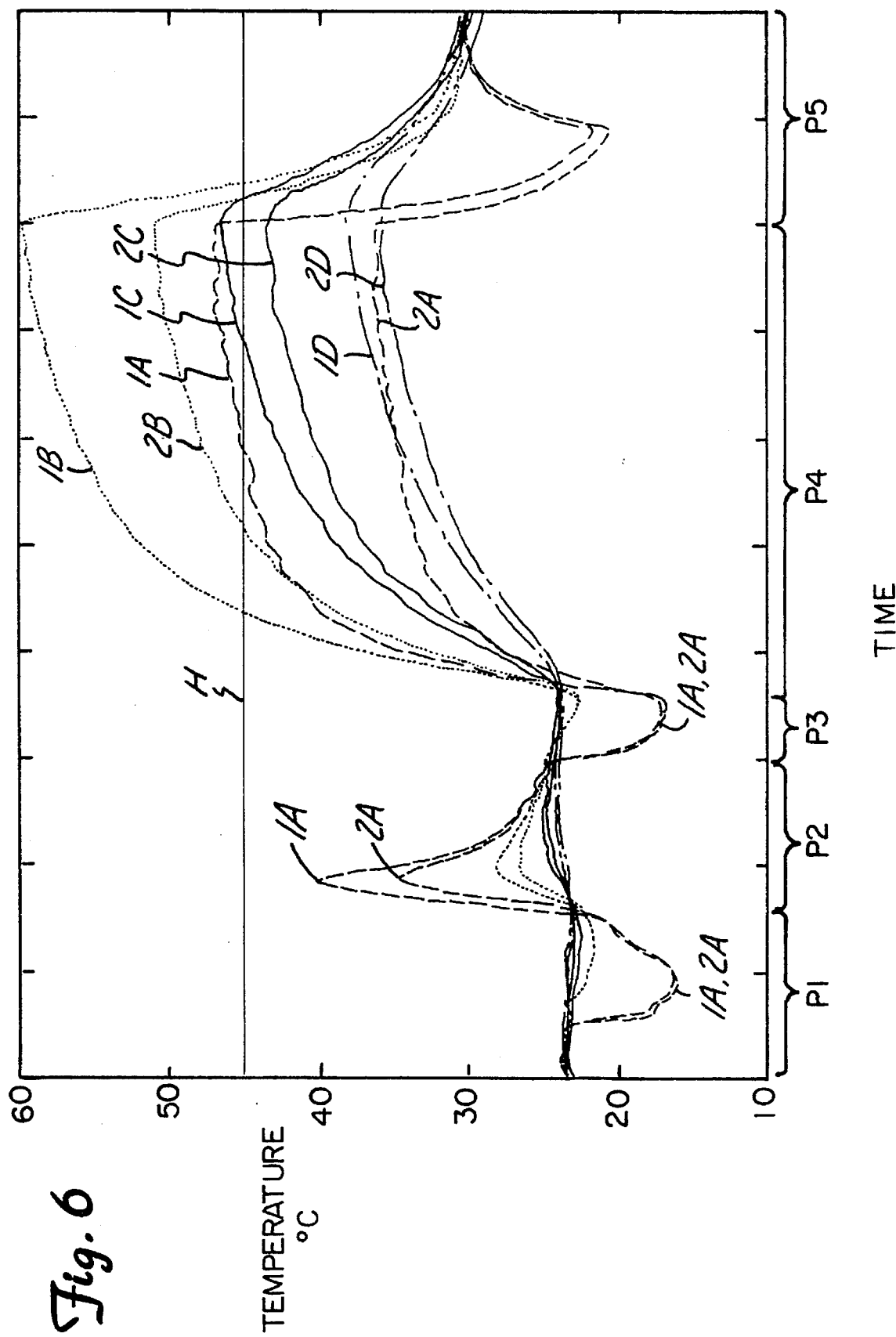
FIG. 6 is a graph illustrating temperature distribution generated by the catheter of the present invention as a function of time.

FIG. 6 is a graph which generally demonstrates a microwave thermal therapy procedure and a temperature distribution which was generated by catheter 28 of the present invention, with shaft 32 inserted into a Polyacrylamide gel formulation which simulates biological tissue. The formulation and preparation procedures for the Polyacrylamide gel are discussed in detail in D. Andreuccetti, M. Bini, A. Ignesti, R. Olmi, N. Rubino, and R. Vanni, *Use of Polyacrylamide as a Tissue-Equivalent Material in the Microwave Range*, 35 IEEE TRANSACTIONS ON BIOMEDICAL ENGINEERING 275 (No. 4, April 1988). FIG. 6 shows temperature measurements taken from eight temperature sensors. Four sensors were aligned at fixed distances adjacent first side 68. Sensor 1A was positioned immediately adjacent shaft 32; sensor 1B was positioned about 0.66 cm from shaft 32; sensor 1C was positioned about 1.33 cm from shaft 32; and sensor 1D was positioned about 2.0 cm from shaft 32.

Four sensors were also aligned at fixed distances adjacent second side 72. Sensor 2A was positioned immediately adjacent shaft 32; sensor 2B was positioned about 0.66 cm from shaft 32; sensor 2C was positioned about 1.33 cm from shaft 32; and sensor 2D was positioned about 2.0 cm from shaft 32.

The x-axis represents a relative period of time over which the microwave thermal therapy procedure was performed. The y-axis represents temperature in degrees Celsius, with horizontal line H representing 45° C. (the temperature at or above which cells are necrosed).

As generally shown in FIG. 6, the microwave thermal therapy procedure of the present invention includes five operating phases, P1–P5. Lines 1A–1D and 2A–2D correspond with sensors 1A–1D and 2A–2D, respectfully. During first phase P1, cooling system 36 is turned on and chilled water is pumped through cooling lumens 64A, 64B and 66A, 66B. A drop in temperature immediately adjacent shaft 32 is represented by lines 1A, 2A. At the end of first phase P1, cooling system 36 is turned off. At the beginning of second phase P2, a relatively small amount of power (about 5 watts) is applied to microwave antenna 74. The temperature immediately adjacent shaft 32 rises asymmetrically due to the greater absorptivity of water in the larger exhaust lumens 66A, 66B on second side 72, as shown by lines 1A, 2A. The power is applied long enough to merely warm adjacent tissue to about 40° C. By the end of second phase P2, temperatures generally return to base line temperature.

In a preferred embodiment of the present invention, the tissue responses to the chilling during P1 and the heating during P2 aid in determining the vascularity of the tissue to be treated. This information aids in determining the amount of power necessary to treat tumorous tissue of prostate 14.

At the beginning of third phase P3, cooling system 36 is again turned on thereby pumping chilled water through cooling lumens 64A–66B. The temperature immediately adjacent shaft 32 correspondingly drops as indicated by lines 1A, 2A. Prechilling of the tissue immediately adjacent shaft 32 aids in protecting the tissues immediately adjacent shaft 32 (i.e., urethra 10) from overheating due to a relatively rapid application of power from antenna 74.

Microwave generating source 38 is again turned on at the beginning of fourth phase P4 at a sustained power output of about 20 watts. As shown in FIG. 6, due to the absorptivity differential between water in the narrower intake lumens 64A, 64B and water in the wider exhaust lumens 66A, 66B, temperatures adjacent second side 72, represented by lines 2A–2D, are cooler than temperatures adjacent first side 68, represented by lines 1A–1D. The temperature differentials are most profound within a target volume of tissue 0.66 cm from shaft 32. Within this target volume, as shown by lines 1A, 2A and 1B, 2B, the difference in temperature from first side 68 and second side 72 is on the order of about 10° C. Thus, by adjusting cooling system parameters or power output from microwave generating source 38, tissue within 0.66 cm of first side 68 can be heated to temperatures at or above about 45° C., while tissue within 0.66 cm of second side 72 can remain at temperatures substantially below 45° C. In this manner, tissue-necrosing temperatures within the target volume are essentially restricted only to tissue near first side 68, which is the most frequent location of periurethral tumorous prostatic tissue. Alternatively, by adjusting the power output or cooling system parameters, a relatively small volume of tissue adjacent second side 72 can be heated above about 45° C. to necrose some of the tumorous prostatic tissue which is posterior and lateral to the urethra. In the preferred embodiment, during fourth phase P4, microwave generating source 38 is operated for at least about 45 minutes.

As shown by lines 1A, 2A, during P4, the temperature of tissue immediately adjacent shaft 32 (which is representative of temperatures of urethra 10), as well as temperatures of tissue beyond 0.66 cm from shaft 32, as shown by lines 1C, 2C and 1D, 2D, are maintainable well below 45° C. This is accomplished by adjusting cooling system parameters and, if necessary, power output from microwave generating source 38.

At the end of fourth phase P4 power is turned off. At the beginning of fifth phase P5, cooling system 36 continues to operate, circulating water through cooling lumens 64A–66B. A temperature drop immediately adjacent shaft 32 is relatively rapid as shown by lines 1A, 2A within P5. In a preferred embodiment of the present invention, cooling system 36 continues to operate for a period of time (on the order of 10 to 120 minutes) after the procedure to cool urethra 10 and reduce edema resulting from the application of heat to the periurethral tissues of prostate 14. In an alternative embodiment, water feed line 94B, water return line 96B and thermometry sensor 69 (as shown in FIG. 2A) are disconnected from connection manifold 35. Water feed line 94B and water return line 96B of catheter 28 are then connected to another cooling system similar to cooling system 36 and water is then circulated through cooling lumens 64A–66B in a manner similar to that previously described. In this fashion, recovery from the previously described procedure can be accomplished away from the treatment area thereby enabling microwave generating source 38 and cooling system 36 to be readily available for treatment of another patient.

Figure 7:
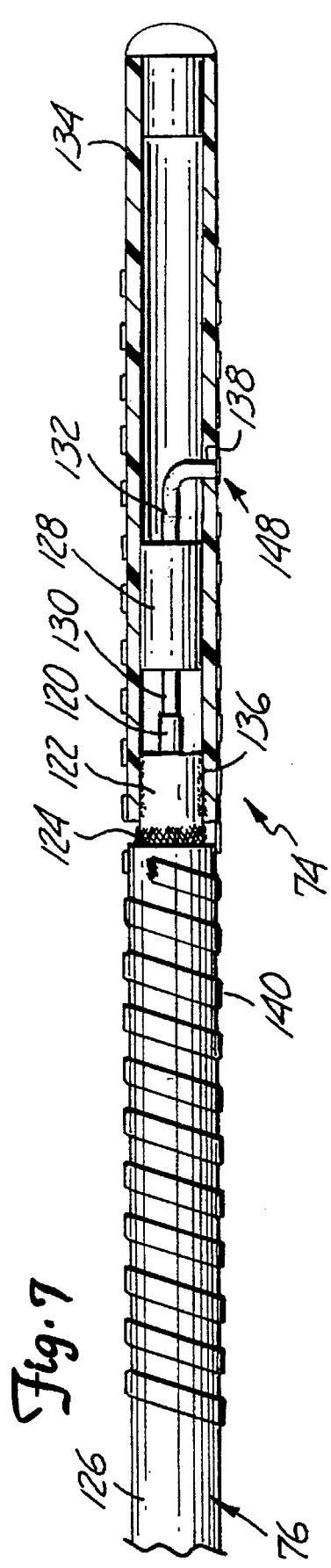
FIG. 7 is a partial sectional view of the microwave antenna of the urethral catheter of the present invention.

FIG. 7 shows a partial sectional view of microwave antenna 74 of the present invention. Antenna 74 is positioned at a proximal-most end of shielded coaxial cable 76. Cable 76 is a standard RG 178U coaxial cable and includes inner conductor 120, inner insulator 122, outer conductor 124, and outer insulator 126. Outer insulator 126, outer conductor 124 and inner insulator 122 are stripped away to expose about 3 millimeters of outer conductor 124, about 1 millimeter of inner insulator 126 and about 1 millimeter of inner conductor 120. Capacitor 128 includes first end 130, which is connected to inner conductor 120 by soldering, and second end 132, which connects to antenna 74. Capacitor 128 serves to counteract a reactive component of antenna 74, thereby providing a 50 ohm match between coaxial cable 76 and microwave generating source 38, and antenna 74.

Tubular extension 134, which is a hollow section of outer insulator 126 of coaxial cable 76, is positioned over capacitor 128 and the exposed length of inner insulator 122 and secured by bond 136. Tubular extension 134 includes hole 138, which provides an exit for second end 132 of capacitor

128. Wound about outer insulator 126 and tubular extension 134 is flat wire 140. Flat wire 140 is a single piece of flat copper wire with dimensions of about 0.009 inch by about 0.032 inch in cross-section, which provides a relatively large surface area for maximum current flow while minimizing the cross-sectional size of antenna 74.

Figure 8:
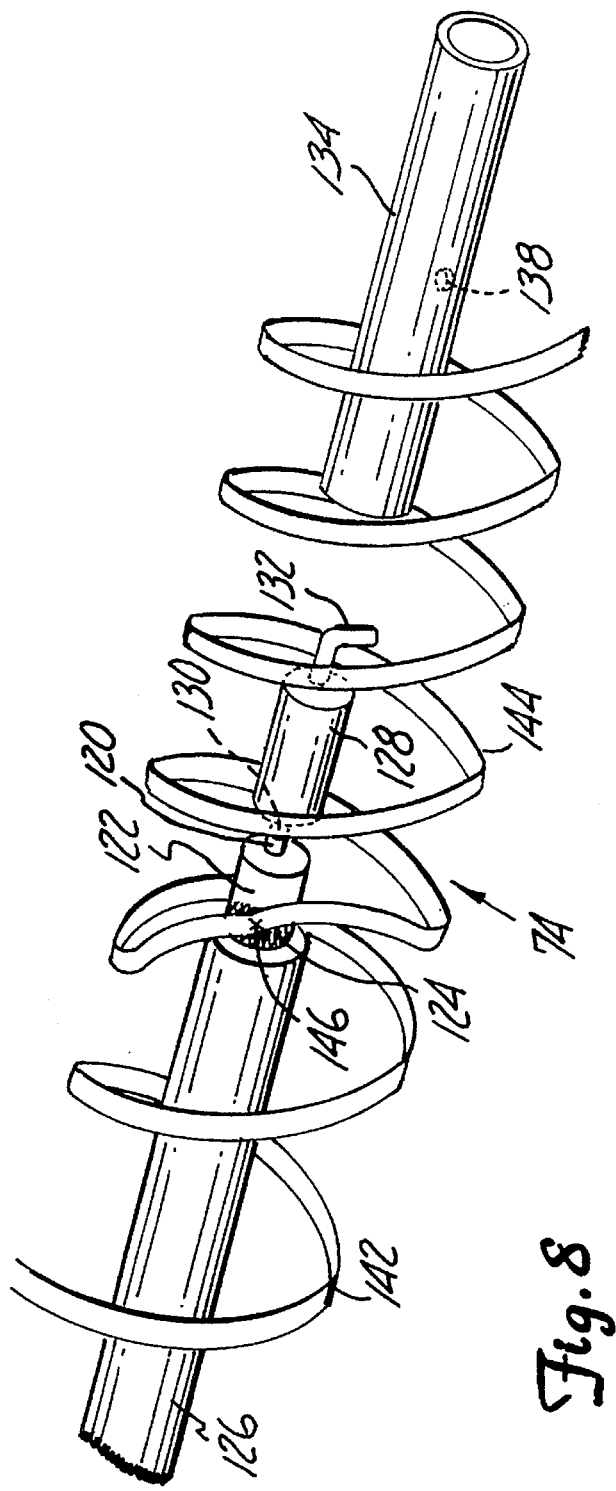
FIG. 8 is an exploded view of the microwave antenna shown in FIG. 7.

FIG. 8 is an exploded view of a portion of antenna 74 which shows its helical dipole construction. Generally, the efficiency of any dipole antenna is greatest when the effective electrical length of the antenna is generally one half the wavelength of the radiation emitted in the surrounding medium. Accordingly, a relatively efficient simple dipole antenna, operating at about 915 MHz, would require a physical length of about 8 centimeters which, according to the present invention, would needlessly irradiate and damage healthy tissue. Furthermore, the physical length of a relatively efficient simple dipole antenna operating at about 915 MHz cannot be varied.

As shown in FIG. 8, flat wire 140 is soldered to outer conductor 124 at solder point 146. Flat wire 140 is then wound in a distal direction about outer insulator 126 and in a proximal direction about tubular extension 134, thereby forming first wire section 142 and second wire section 144, both of which are of equal length. In one embodiment, first and second wire sections 142 and 144 are each comprised of eight, equally-spaced windings of flat wire 140. The combined length of first and second wire sections 142 and 144, and hence the overall length of antenna 74, ranges from about 1.5 centimeters to about 4.0 centimeters, and varies according to the length of the area of prostate 14 which requires treatment. A standard medical-grade silicone tube (not shown), which has been allowed to soak in a solvent, such as Freon, is positioned over first and second wire sections 142 and 144. As the solvent evaporates, the silicone tube shrinks, thereby securing flat wire 140 to outer insulator 126 and tubular extension 134.

The helical dipole construction of the present invention, allows antenna 74 to range in physical length from about 1.5 to 4 centimeters, while electrically behaving like an eight centimeter-long simple dipole antenna. In other words, antenna 74 has an effective electrical length generally equal to one half of the wavelength of the radiation emitted in the surrounding medium, independent of its physical length. For purposes of definition, the surrounding medium includes the catheter shaft and the surrounding tissue. This is accomplished by varying the number and pitch of the windings of first and second wire sections 142 and 144. A family of catheters, which contain relatively efficient helical dipole antennas of different physical lengths, permits selection of the antenna best suited for the particular treatment area. In addition, antenna 74 of the present invention is capable of producing a constant heating pattern in tissue, concentrated about antenna 74, independent of the depth of insertion into the tissue.

Second end 132 of capacitor 128, which exits hole 138, is soldered to second wire section 144 at tap point 148, as shown in FIG. 7. Tap point 148 is a point at which the resistive component of the combined impedance of first wire section 142 and second wire section 144 matches the characteristic impedance of coaxial cable 76. The impedance of either first wire section 142 or second wire section 144 is expressed as Z, where $Z=R+jX$. The impedance Z varies from a low value at solder point 146 to a high value at a point farthest from solder point 146. There exists a tap position where R is equal to 50 ohms, but an imaginary component, X, is inductive. This inductive component can be canceled by inserting a series capacitance, such as capacitor 128, which has a value of $-jX$ ohms. This results in an impedance match of 50 ohms real. The resulting method of feeding antenna 74 is commonly called gamma matching. In one embodiment of the present invention, where the physical length of flat wire 140 is about 2.8 cm, tap point 148 is about 3.5 turns from solder point 146 on second wire section 144. In the preferred embodiment, the value of capacitor 128 is about 2.7 pF.

The helical dipole construction of antenna 74 achieves a relatively small size, which permits intraurethral application. The helical dipole construction is also responsible for three features which enable antenna 74 to achieve greater efficiency than prior known interstitial microwave antennas: good impedance matching, good current carrying capability and an effective electrical length which is generally one half of the wavelength of the radiation emitted in the surrounding medium, independent of the physical length of antenna 74.

First, the good impedance match between antenna 74 and inner conductor 120 minimizes reflective losses of antenna 74, with measured reflective losses of less than 1% in a preferred embodiment. Second, the use of flat ribbon wire 140 for first wire section 142 and second wire section 144 minimizes resistive losses of antenna 74 by providing a greater surface area upon which RF current can be carried. Finally, the helical dipole design of antenna 74 has an effective electrical length which is generally one half of the wavelength of the radiation emitted in the surrounding medium, independent of the physical length of antenna 74. This permits the physical length of antenna 74 to be varied to accommodate varying sizes of individual prostates while maintaining the same efficient, effective electrical length of antenna 74.

The use of an efficient microwave antenna is critical to the ability to focus thermal energy a distance from the antenna within a target volume. An inefficient antenna produces a lesser intensity of microwave radiation within the target volume than desired. It also produces undesired heat close to the urethra, which will damage the urethra if not carried away by an increased coolant flow. This added burden on the cooling system reduces its capacity to protect the urethra, thereby limiting the microwave power that can be radiated without elevating urethra temperatures above safety limits. With microwave power limited by cooling system capacity, the heat delivered to the desired target area of the prostate will not be sufficient for effective therapy. The efficient helical dipole design of antenna 74 of the present invention, however, ensures that almost all heat delivered during the treatment is delivered in the form of microwave energy, rather than conductive heat energy.

FIG. 9 is a block diagram of transurethral microwave thermal therapy system 170, with which urethral catheter 28 is used. System 170 includes cooling system 36 microwave generating source 38, user interface 172, real time controller (RTC) 174, directional coupler 176, thermometry sensors 182 and 184, coolant pressure sensor 186, balloon inflation device 188, and urine collection container 190.

As shown in FIG. 9, control of microwave generating source 38 and cooling system 36 is effected by real time controller 174, which is in turn controlled by user interface 172. User interface 172 is an IBM compatible machine containing two hard drives for data storage: one for backup, and one for normal operation of system 170. User interface 172 communicates with RTC 174, which is responsible for all closed loop feedback to run system 170. RTC 174 has direct closed loop control of microwave power from microwave generating source 38, and coolant flow and coolant temperature of cooling system 36. Closed loop feedback tracks out variations in gain, drift and cable losses inherent in microwave generating source 38, and variability in pump output and refrigeration system efficiency of cooling system 36. In addition to monitoring microwave generating source 38 and cooling system 36, RTC 174 also monitors and controls several channels of thermometry via inputs from thermometry unit 178. Cooling system thermometry 178A measures the coolant and chiller temperatures based upon signals from coolant temperature sensors 182 and 184 and a chiller temperature sensor (not shown) of cooling system 36. Urethral thermometry 178B measures urethral temperature based upon signals from temperature sensor 69 within catheter 28. Rectal thermometry 178C measures rectal temperature based upon signals received from a sensor (not shown) within rectal probe 180.

RTC 174 transmits all closed-loop feedback to user interface 172, which processes the input and transmits corrections and instructions back to RTC 174. RTC 174 interprets the instructions given to it by process control language received from user interface 172 and executes the instructions in real time. All corrections from user interface 172 are made to maintain a given thermal profile throughout the transurethral thermal therapy. In addition, system 170 includes a hardware fail-safe circuit which shuts down system 170 should any parameter fall outside a given range of values.

While the beneficial uses of the microwave antenna-containing catheter of the present invention have been described with respect to the urethra, other intracavitary applications are implied.

Although the present invention has been described with reference to preferred embodiments, workers skilled in the art will recognize that changes may be made in form and detail without departing from the spirit and scope of the invention.

What is claimed is:

1. A device for administering therapy to a prostate comprising:

a urological catheter; and heating means within the catheter for selectively delivering heat to the prostate, wherein the heating means is capable of delivering a first amount of heat in a first radial direction which is greater than a second amount of heat in a second radial direction.

2. A device for administering thermal therapy to prostatic tissue comprising:

a urological catheter;

heating means within the catheter for selectively heating the prostatic tissue, the heating means capable of delivering heat in a first volume of prostatic tissue which is greater than that delivered to a second volume of prostatic tissue.

3. An intraurethral device for treating a prostate comprising:

a urological catheter; and electromagnetic energy emitting means within the catheter for selectively directing electromagnetic energy into the prostate, the electromagnetic energy emitting means capable of delivering first amount of energy in a first radial direction relative to the catheter which is greater than a second amount of energy delivered in a second radial direction relative to the catheter.

4. A method of treating the prostate comprising:

inserting into a urethra a urological catheter which contains a heating system;

activating the heating system to produce a first amount of heat in a first radial volume of the prostate and to produce a second amount of heat in a second radial volume of the prostate, the first amount of heat being greater than the second amount of heat.

\* \* \* \* \*